US011903769B2

United States Patent
Li et al.

(10) Patent No.: US 11,903,769 B2
(45) Date of Patent: Feb. 20, 2024

(54) FIRST-ORDER ESTIMATION METHOD OF SHEAR WAVE VELOCITY

(71) Applicant: SHANTOU INSTITUTE OF ULTRASONIC INSTRUMENTS CO., LTD., Guangdong (CN)

(72) Inventors: Delai Li, Guangdong (CN); Liexiang Fan, Guangdong (CN); Yinan Huang, Guangdong (CN); Bin Li, Guangdong (CN)

(73) Assignee: SHANTOU INSTITUTE OF ULTRASONIC INSTRUMENTS CO., LTD., Guangdong (CN)

( * ) Notice: Subject to any disclaimer, the term of this patent is extended or adjusted under 35 U.S.C. 154(b) by 255 days.

(21) Appl. No.: 17/411,751

(22) Filed: Aug. 25, 2021

(65) Prior Publication Data

US 2021/0378636 A1    Dec. 9, 2021

Related U.S. Application Data

(63) Continuation of application No. PCT/CN2019/116431, filed on Nov. 8, 2019.

(30) Foreign Application Priority Data

Oct. 31, 2019    (CN) .......................... 201911051147.2

(51) Int. Cl.
*A61B 8/08*    (2006.01)

(52) U.S. Cl.
CPC .................................... *A61B 8/485* (2013.01)

(58) Field of Classification Search
CPC ...................................................... A61B 8/485
See application file for complete search history.

(56) References Cited

FOREIGN PATENT DOCUMENTS

| CN | 103431874 A | 12/2013 |
|----|-------------|---------|
| CN | 103519848 A | 1/2014 |
| CN | 104546014 A | 4/2015 |
| CN | 104739451 A | 7/2015 |
| CN | 105212961 A | 1/2016 |
| CN | 107616814 A | 1/2018 |
| CN | 109589138 A | 4/2019 |
| JP | 2013102959 A | 5/2013 |
| WO | WO-2019179758 A1 | 9/2019 |

*Primary Examiner* — Colin T. Sakamoto
(74) *Attorney, Agent, or Firm* — MUNCY, GEISSLER, OLDS & LOWE, P.C.

(57) ABSTRACT

A first-order estimation method of shear wave velocity, includes the steps of demodulating entry data, and obtaining a complex angle value, matrix average, offset matrix, displacement matrix and shear wave velocity. According to the method, the main contour of the displacement curve is extracted by the quadrature decomposition of matrix, thereby improving the signal quality of the shear wave estimation. Unlike conventional method which needs estimating twice, the shear wave displacement curve can be estimated directly to reduce estimation errors and improve estimation efficiency.

7 Claims, 4 Drawing Sheets

$$\begin{bmatrix} 3.5894+0.0003i & 3.3804+0.0002i & 3.3800+0.0002i & 3.3649+0.0002i & 3.3233+0.0000i & 3.3418-0.0002i & 3.3835+0.0001i & 3.3650+0.0003i & 3.3659+0.0003i \\ 2.0198-0.0013i & 2.0139-0.0013i & 2.0196-0.0013i & 2.0073-0.0013i & 1.8600-0.0014i & 1.8566-0.0015i & 1.9994-0.0014i & 2.0382-0.0012i & 2.0344-0.0013i \\ 0.3981+0.0008i & 0.4011+0.0008i & 0.3756+0.0008i & 0.4686+0.0009i & 0.5371+0.0008i & 0.4719+0.0008i & 0.3979+0.0008i & 0.3781+0.0008i & 0.3921+0.0008i \\ 1.3173+0.0002i & 1.3200+0.0002i & 1.3138+0.0002i & 1.2204-0.0000i & 1.3273+0.0000i & 1.3273+0.0002i & 1.3089+0.0003i & 1.3004+0.0003i & 1.3041+0.0002i \end{bmatrix}$$

FIG. 1

$$\begin{bmatrix} 0.0786 & 0.0733 & 0.0682 & 0.0521 & 0.0068 & -0.0680 & 0.0319 & 0.0943 & 0.0856 \\ -0.5822 & -0.5810 & -0.5732 & -0.5800 & -0.6550 & -0.6889 & -0.5965 & -0.5500 & -0.5562 \\ 1.1252 & 1.1211 & 1.1449 & 1.0734 & 0.9819 & 1.0489 & 1.1224 & 1.1451 & 1.1318 \\ 0.1651 & 0.1653 & 0.1863 & -0.0351 & 0.0042 & 0.1440 & 0.2091 & 0.1971 & 0.1781 \end{bmatrix}$$

FIG. 2

$$\begin{bmatrix} 0.0470 \\ -0.5959 \\ 1.0994 \\ 0.1349 \end{bmatrix}$$

FIG. 3

| 0.0470 | 0.0470 | 0.0470 | 0.0470 | 0.0470 | 0.0470 | 0.0470 | 0.0470 | 0.0470 |
| -0.5959 | -0.5959 | -0.5959 | -0.5959 | -0.5959 | -0.5959 | -0.5959 | -0.5959 | -0.5959 |
| 1.0994 | 1.0994 | 1.0994 | 1.0994 | 1.0994 | 1.0994 | 1.0994 | 1.0994 | 1.0994 |
| 0.1349 | 0.1349 | 0.1349 | 0.1349 | 0.1349 | 0.1349 | 0.1349 | 0.1349 | 0.1349 |

FIG. 4

| 0.0317 | 0.0263 | 0.0212 | 0.0051 | -0.0402 | -0.1150 | -0.0151 | 0.0473 | 0.0386 |
| 0.0137 | 0.0149 | 0.0227 | 0.0159 | -0.0591 | -0.0930 | -0.0006 | 0.0459 | 0.0396 |
| 0.0258 | 0.0217 | 0.0455 | -0.0260 | -0.1175 | -0.0505 | 0.0230 | 0.0457 | 0.0324 |
| 0.0302 | 0.0304 | 0.0514 | -0.1700 | -0.1307 | 0.0091 | 0.0742 | 0.0622 | 0.0432 |

FIG. 5

| -0.3039 | -0.6081 | 0.5690 | -0.4627 |
| -0.3022 | -0.5204 | -0.0707 | 0.7955 |
| -0.4905 | -0.1847 | -0.7645 | -0.3752 |
| -0.7587 | 0.5703 | 0.2946 | 0.1110 |

FIG. 6

| 0.2979 | 0 | 0 | 0 | 0 | 0 | 0 | 0 | 0 |
|---|---|---|---|---|---|---|---|---|
| 0 | 0.1796 | 0 | 0 | 0 | 0 | 0 | 0 | 0 |
| 0 | 0 | 0.0496 | 0 | 0 | 0 | 0 | 0 | 0 |
| 0 | 0 | 0 | 0.0154 | 0 | 0 | 0 | 0 | 0 |

FIG. 7

| -0.1656 | -0.0775 | 0.1257 | -0.6553 | 0.3007 | 0.5959 | 0.2290 | -0.1447 | -0.0500 |
|---|---|---|---|---|---|---|---|---|
| -0.1551 | 0.0582 | 0.1264 | -0.3299 | -0.5327 | -0.2042 | 0.4224 | 0.3778 | 0.4485 |
| -0.2505 | -0.0213 | -0.1843 | -0.2033 | 0.6883 | -0.5163 | -0.0523 | 0.1781 | 0.2946 |
| 0.4544 | -0.5764 | -0.5718 | 0.0766 | 0.0759 | 0.1695 | 0.2436 | 0.1474 | 0.1137 |
| 0.6276 | 0.0132 | 0.6589 | 0.0722 | 0.3042 | -0.0571 | 0.1775 | 0.1555 | 0.1234 |
| 0.2718 | 0.7397 | -0.3538 | -0.0516 | 0.0367 | 0.2959 | -0.0869 | 0.2810 | 0.2751 |
| -0.2110 | 0.2649 | -0.0861 | 0.3984 | 0.1788 | -0.0133 | 0.8026 | -0.1392 | -0.1536 |
| -0.3285 | -0.1425 | 0.1416 | 0.2832 | 0.1248 | 0.3142 | -0.0976 | -0.7712 | -0.2301 |
| -0.2431 | -0.1419 | 0.1434 | 0.4097 | 0.0702 | 0.3439 | -0.1202 | -0.2561 | 0.7274 |

FIG. 8

$$\begin{pmatrix} 0.2979 & 0 & 0 & 0 & 0 & 0 & 0 & 0 & 0 & 0 \\ 0 & 0.1796 & 0 & 0 & 0 & 0 & 0 & 0 & 0 & 0 \\ 0 & 0 & 0 & 0 & 0 & 0 & 0 & 0 & 0 & 0 \\ 0 & 0 & 0 & 0 & 0 & 0 & 0 & 0 & 0 & 0 \end{pmatrix}$$

FIG. 9

$$\begin{pmatrix} 0.0235 & 0.0204 & 0.0250 & 0.0218 & -0.0582 & -0.1054 & -0.0098 & 0.0453 & 0.0375 \\ 0.0221 & 0.0194 & 0.0245 & 0.0130 & -0.0577 & -0.0936 & -0.0058 & 0.0429 & 0.0351 \\ 0.0268 & 0.0246 & 0.0373 & -0.0473 & -0.0921 & -0.0643 & 0.0221 & 0.0527 & 0.0402 \\ 0.0295 & 0.0291 & 0.0544 & -0.1617 & -0.1405 & 0.0143 & 0.0748 & 0.0596 & 0.0404 \end{pmatrix}$$

FIG. 10

FIRST-ORDER ESTIMATION METHOD OF SHEAR WAVE VELOCITY

CROSS REFERENCE TO RELATED APPLICATIONS

The present application is a continuation of International Application No. PCT/CN2019/116431, filed on Nov. 8, 2019, which claims priority from Chinese Patent Application No. 201911051147.2 filed on Oct. 31, 2019, all of which are hereby incorporated herein by reference.

TECHNICAL FIELD

The present invention relates to the technical field of ultrasonic shear wave elasticity imaging, and more particularly relates to a first-order estimation method of shear wave velocity.

BACKGROUND

Medical ultrasound equipment evaluates tissue hardness by measuring the movement speed of shear wave in human tissue. This technology is used in various diagnostic applications, such as evaluating liver diseases. Shear wave velocity can characterize tissue hardness characteristics to allow detection of tumors or other parts.

The conventional method of calculating shear wave velocity is:

converting an ultrasonic echo signal of a specific point into digital echo data by an ultrasonic probe and ultrasonic equipment, in which, the ultrasonic echo signal is firstly converted into an electrical signal by the ultrasonic probe, then the electrical signal is converted into digital echo data which can be processed by computers by the ultrasonic equipment through amplification, analog-to-digital conversion, ultrasonic beam forming and other process;

obtaining an instantaneous velocity of a particle by the echo data information, in which the method of obtaining instantaneous velocity is similar to the principle of ultrasonic detection of blood flow velocity;

calculating a curve of longitudinal displacement $\int_0^T v_f(t)dt$ by using the instantaneous velocity $v_f(t)$;

obtaining the displacement curve of multiple positions and calculating the shear wave velocity $v_f(t)$ through the information of position and time of the curve.

The above method needs to calculate the instantaneous velocity $v_f(t)$ of the particle at first, then calculate the displacement $\int_0^T v_f(t)dt$, and finally calculate the shear wave velocity $v_s(t)$. The calculation process is complicated, and the calculated displacement curve is susceptible to the signal-to-noise ratio of the ultrasonic signal and the human motion, resulting in inaccurate and poor stable shear wave velocity.

SUMMARY

The present invention provides a first-order estimation method that can efficiently and accurately estimate the shear wave velocity.

According to the present invention, the first-order estimation of shear wave velocity includes the following steps.

Entry data is demodulated. During an ultrasonic inspection process, an ultrasonic echo signal is converted into an electrical signal by an ultrasonic probe, and the electrical signal is converted into digital echo data by an ultrasonic equipment. In this step, a data matrix is formed with different echo data obtained at different scanning positions and different scanning times during the ultrasonic inspection process. And the data matrix is formed to an entry matrix $I_1$ based on IQ data in complex form by a quadrature modulation.

Angle value of the complex IQ data is calculated. The angle value of the complex IQ data of each data point of the matrix $I_1$ demodulated by the entry data is calculated, and a real number of the corresponding data point is obtained to form an angle value matrix $I_2$.

An average evaluation of the angle value matrix is obtained. In this step, the real average value of all data at the same scanning position of the angle value matrix $I_2$ is calculated to obtain a single-column mean value matrix $I_3$.

An offset matrix is obtained. In this step, a matching matrix $I_4$ is introduced. The matching matrix $I_4$ is a single-row matrix which has the same columns as the angle value matrix $I_2$ and its data point values are all real numbers "1". The mean matrix $I_3$ is multiplied by the matching matrix $I_4$ to obtain the offset matrix $I_5$.

A displacement matrix is obtained. In this step, by the mutual operations of the angle value matrix $I_2$ and the offset matrix $I_5$, the displacement matrix $I_6$ is obtained. The displacement matrix $I_6$ is the displacement value of the particle that changes with time in the propagation of the shear wave.

The shear wave velocity is calculated. In this step, the data of the displacement matrix $I_6$ is formed into multiple sets of displacement curves on the coordinate axis, and the highest point of each displacement curve is taken to calculate the shear wave velocity $V_s(t)$.

In the step of entry data demodulation, the matrix rows of the data matrix are echo information of different scanning positions; and the matrix columns are echo information at the same position at different scanning times.

In the coordinate system where the displacement curve is located, the ordinate is distance, and the abscissa is time.

The expression of the data points of the entry matrix $I_1$ is $Z_n = a_n + b_n * j$, and the solution formula of the data points of the angle value matrix $I_2$ is $A_n = \sin^{-1}(b_n/a_n)$.

In the formula of the shear wave velocity, $V_s(t) = s_n/t_n$, $s_n$ is the distance difference between the highest point of each displacement curve in each set of displacement curves, and $t_n$ is the corresponding time difference between the highest point of each displacement curve in each set of displacement curves.

The method further includes the following steps.

The displacement curve is decomposed and reconstructed. After the singular value decomposition of the displacement matrix $I_6$, a construction matrix $I_7$ is obtained based on the singular value matrix obtained by the decomposition.

Specifically, the formula for solving the reconstruction matrix $I_7$ is $I_7 = U * S * V$. In this formula, U is a left singular matrix, V is a right singularity Matrix and S is a diagonal matrix containing singular values.

According to the present invention, the first-order estimation of the shear wave velocity extracts the main contour of the displacement curve by the orthogonal decomposition of matrix, thereby improving the signal quality of the shear wave estimation. And unlike conventional method, which needs estimating twice, the present invention can estimate the shear wave's displacement curve directly to reduce estimation errors and improve estimation efficiency.

BRIEF DESCRIPTION OF THE DRAWINGS

The invention can be more fully understood by reading the subsequent detailed description and examples with references made to the accompanying drawings, wherein:

FIG. 1 shows an entry matrix formed from data matrix;

FIG. 2 shows an angle value matrix of a 4 by 9 array according to an embodiment;

FIG. 3 shows a mean matrix of a 1 by 4 array according to an embodiment;

FIG. 4 shows an offset matrix that is a product of the mean matrix and a matching matrix according to an embodiment;

FIG. 5 shows a displacement matrix that determines a displacement value of a particle according to an embodiment;

FIG. 6 shows a 4 by 4 array matrix indicating a left singular matrix according to an embodiment;

FIG. 7 shows a 4 by 4 array matrix indicating a diagonal matrix according to an embodiment;

FIG. 8 shows a 9 by 9 matrix indicating a right singular matrix according to an embodiment;

FIG. 9 shows two singular values of the diagonal matrix shown in FIG. 7 according to an embodiment; and FIG. 10 is a reconstruction matrix obtained in a reconstruction process according to an embodiment.

DETAILED DESCRIPTION OF THE EMBODIMENT

The invention will be described in detail with embodiments.

A first-order estimation method of shear wave velocity in an embodiment of the invention takes a complex matrix of a 4 by 9 array as the entry matrix $I_1$ as an example. The specific operation process is as follows.

First is the entry data demodulation. A data matrix is formed with different echo data obtained at different scanning positions and different scanning times during the ultrasonic inspection process. And then the data matrix is formed to an entry matrix $I_1$ by a quadrature modulation. The entry matrix $I_1$ takes IQ data in complex form as data points. Specifically, in demodulation, the matrix rows of the data matrix are echo information of different scanning positions; and the matrix columns are echo information at the same position at different scanning times. The obtained entry matrix $I_1$ is shown in FIG. 1.

Then the angle value of the entry matrix $I_1$ is calculated. The angle value of the complex IQ data of each data point of the matrix $I_1$ demodulated by the entry data is calculated, and the real number of the corresponding data point is obtained to form an angle value matrix $I_2$. The expression of the data points of the entry matrix $I_1$ is $Z_n=a_n+b_n*j$, and the solution formula of the data points of the angle value matrix $I_2$ is $$A_n = \sin^{-1}(b_n/a_n).$$

The obtained angle value matrix $I_2$ of the 4 by 9 array in this embodiment is shown in FIG. 2, and its data points are all real numbers.

The average of the matrix based on the angle value matrix $I_2$ is obtained. In this step, the average value of all data at the same scanning position of the angle value matrix $I_2$ is calculated to obtain a single-column mean value matrix $I_3$. The average calculation method is conventional, which is to calculate the average value of all data in the same column. For this embodiment, for the above column contains 9 data, the formula of average value of the column is $m=(i_1+i_2+\ldots i_9)/9$ Specifically, the mean matrix $I_3$ of the 1 by 4 array in this embodiment is obtained as shown in FIG. 3.

An offset matrix on the base of mean matrix $I_3$ is obtained. In this step, a matching matrix $I_4$ is introduced. The matching matrix $I_4$ is a single-row matrix which has the same columns as the angle value matrix $I_2$ and its data point values are all real numbers "1". The mean matrix $I_3$ is multiplied by the matching matrix $I_4$ to obtain the offset matrix $I_5$.

That is, the offset matrix $I_5$ is the product of the mean matrix $I_3$ and the matching matrix $I_4$. The specific offset matrix $I_5$ in this embodiment is shown in FIG. 4.

By mutual operations of the angle value matrix $I_2$ and the offset matrix $I_5$, a displacement matrix $I_6$ is obtained. The displacement matrix $I_6$ is the displacement value of the particle that changes with time in the propagation of the shear wave. Actual displacement matrix $I_6$ is the difference between the angle value matrix $I_2$ and the offset matrix $I_5$. That is, the corresponding data points of the matrix are performed operation to obtained the displacement matrix $I_6$. The displacement matrix $I_6$ of the present embodiment is as shown in FIG. 5.

The shear wave velocity is calculated by the displacement matrix $I_6$. In this step, the data of the displacement matrix $I_6$ is formed into multiple sets of displacement curves on the coordinate axis, and the highest point of each displacement curve is taken to calculate the shear wave velocity $V_s(t)$. In the coordinate system where the displacement curve is located, the ordinate is distance, and the abscissa is time. In the formula of the shear wave velocity, $$V_s(t) = S_n/t_n,$$

$s_n$ is the distance difference between the highest point of each displacement curve in each set of displacement curves, $t_n$ is the corresponding time difference between the highest point of each displacement curve in each set of displacement curves.

After the shear wave velocity is obtained, an orthogonal decomposition and reconstruction of the displacement curve can be performed to further remove the noise of the displacement curve, and keep the most critical message of the displacement curve, so as to make displacement curve more precise and the final estimation more accurate. Specifically, it includes the following steps.

The displacement curve is decomposed and reconstructed. After the singular value decomposition of the displacement matrix $I_6$, a construction matrix $I_7$ is obtained based on the singular value matrix obtained by the decomposition.

After performing singular value decomposition on the displacement matrix $I_6$, a left singular matrix U, a diagonal matrix S containing the singular values and a right singular matrix V can be obtained.

The left singular matrix U in the present embodiment is a 4 by 4 array matrix, as shown in FIG. 6:

The diagonal matrix S of the singular values in the present embodiment is a 4 by 9 matrix, as shown in FIG. 7:

The right singular matrix V in the present embodiment is a 9 by 9 matrix, as shown in FIG. 8:

Specifically, the solution formula of the reconstruction matrix $I_7$ is $I_7=U*S_0*V^T$, in which $S_0$ is the diagonal matrix based on the first two singular values, and $V^T$ is the right singular matrix based on the first 4 columns, as shown in FIG. 9.

The reconstruction matrix $I_7$ after reconstruction in the present embodiment is as shown in FIG. 10:

Compared with the unreconstructed displacement matrix $I_6$, the reconstructed reconstruction matrix $I_7$ can obtain a smoother and more consistent displacement curve, which can in turn obtain a more accurate shear wave velocity $V_s(t)$. The method of directly estimating the particle displacement curve based on the complex matrix constructed from the original data and improving the estimation accuracy of velocity by matrix reconstruction is called first-order estimation.

The above content is a further detailed description of the invention with specific preferred embodiments. It cannot be considered that the specific embodiment of this invention is limited to these descriptions. For those skilled in the art, simple deductions or substitutions which can be made without departing from the concept of the invention, should be regarded that it is within the protection scope of the present invention.

What is claimed is:

1. A first-order estimation method of shear wave velocity, comprising the steps of:
    demodulating entry data, comprising the steps of:
        during an ultrasonic inspection process, converting an ultrasonic echo signal into an electrical signal by an ultrasonic probe, and converting the electrical signal into digital echo data by an ultrasonic equipment,
        forming a data matrix with different echo data obtained at different scanning positions and different scanning times during the ultrasonic inspection process, and
        forming the data matrix into an entry matrix $I_1$ by a quadrature modulation by taking IQ data in complex form as data points;
    calculating an angle value of the IQ data in complex form, comprising the steps of:
        calculating the angle value of the complex IQ data of each data point of the matrix $I_1$, and obtaining a real number of the corresponding data point to form an angle value matrix $I_2$;
    calculating a real average value of the angle value matrix, comprising the steps of:
        calculating the real average value of all data at the same scanning position of the angle value matrix $I_2$ to obtain a single-column mean value matrix $I_3$;
    obtaining an offset matrix, comprising the steps of:
        introducing a matching matrix $I_4$, wherein the matching matrix $I_4$ is a single-row matrix which has the same columns as the angle value matrix $I_2$ and its data point values are all real numbers "1", and obtaining an offset matrix $I_5$ by multiplying the single-column mean value matrix $I_3$ and the matching matrix $I_4$;
    obtaining a displacement matrix, comprising the steps of:
        by mutual operations of the angle value matrix $I_2$ and the offset matrix $I_5$, obtaining the displacement matrix $I_6$ which is a displacement value of a particle that changes with time in a propagation of a shear wave;
    calculating shear wave velocity, comprising the steps of:
        forming the data of the displacement matrix $I_6$ into multiple sets of displacement curves on a coordinate axis, and a highest value point of each displacement curve is taken to calculate the shear wave velocity $V_s(t)$.

2. The first-order estimation method of shear wave velocity according to claim 1, wherein in the step of demodulation of the entry data, matrix row index of the data matrix presents different scanning positions of echo information; and matrix column index present different scanning times at the same position of echo information.

3. The first-order estimation method of shear wave velocity according to claim 2, wherein in a coordinate system where the displacement curve is located, an ordinate is distance, and an abscissa is time.

4. The first-order estimation method of shear wave velocity according to claim 2, wherein an expression of the data points of the entry matrix $I_1$ is $Z_n=a_n+b_n*1j$, where j indicates an imaginary part of the expression, and a solution formula of the data points of the angle value matrix $I_2$ is $A_n=\sin^{-1}(b_n/a_n)$.

5. The first-order estimation method of shear wave velocity according to claim 4, wherein the shear wave velocity is calculated from: $V_s(t)=s_n/t_n$, in which $s_n$ is a distance difference between the highest point of each displacement curve in each set of displacement curves and $t_n$ is a corresponding time difference between the highest point of each displacement curve in each set of displacement curves.

6. The first-order estimation method of shear wave velocity according to claim 1, further comprising the steps of:
    decomposing and reconstructing the displacement curve, comprising the step of:
        after a singular value decomposition of the displacement matrix $I_6$, obtaining a reconstruction matrix $I_7$ based on a singular value matrix obtained by the decomposition.

7. The first-order estimation method of shear wave velocity according to claim 6, wherein the reconstruction matrix $I_7$ is obtained from $I_7=U*S*V$, in which U is a left singular matrix, V is a right singularity matrix and S is a diagonal matrix containing singular values.

* * * * *